(12) United States Patent
Fischer et al.

(10) Patent No.: US 7,115,276 B1
(45) Date of Patent: Oct. 3, 2006

(54) PATCH WITH REDUCED COLD FLOW

(75) Inventors: Wilfried Fischer, Munich (DE); Hubert Kaffl, Munich (DE); Petra Huber, Munich (DE); Clifton Zimmermann, Munich (DE)

(73) Assignee: Novosis AG, Munich (DE)

( * ) Notice: Subject to any disclaimer, the term of this patent is extended or adjusted under 35 U.S.C. 154(b) by 0 days.

(21) Appl. No.: 09/602,440

(22) Filed: Jun. 23, 2000

(30) Foreign Application Priority Data

Jun. 25, 1999 (DE) .................................. 299 11 111

(51) Int. Cl.
*A61K 9/70* (2006.01)
*A61L 15/00* (2006.01)
*A61L 15/16* (2006.01)
*A01N 25/34* (2006.01)

(52) U.S. Cl. .................... 424/443; 424/445; 424/447; 424/448; 424/449; 424/402

(58) Field of Classification Search ................ 424/443, 424/445, 447, 402, 448, 449
See application file for complete search history.

(56) References Cited

U.S. PATENT DOCUMENTS

| | | | | |
|---|---|---|---|---|
| 5,264,218 A | * | 11/1993 | Rogozinski | 424/445 |
| 5,415,866 A | * | 5/1995 | Zook | 424/448 |
| 5,538,736 A | * | 7/1996 | Hoffmann et al. | 424/448 |
| 5,633,007 A | * | 5/1997 | Webb et al. | 424/443 |
| 5,695,779 A | * | 12/1997 | Mori | |
| 5,714,225 A | * | 2/1998 | Hansen et al. | 428/114 |

* cited by examiner

*Primary Examiner*—Humera N. Sheikh
(74) *Attorney, Agent, or Firm*—Frommer Lawrence & Haug LLP; Ronald R. Santucci

(57) ABSTRACT

The present invention refers to a flat self-adhering plaster having a multi-layer construction and reduced cold flow, characterized in that the layer of adhesive possesses a core of adhesive being a flowable adhesive and a ring of adhesive being an adhesive having reduced flowability which surrounds the core.

9 Claims, No Drawings

PATCH WITH REDUCED COLD FLOW

This application claims benefit of foreign priority to German Application No. 299 11 111.3 filed Jun. 25, 1999.

FIELD OF THE INVENTION

The invention refers to a plaster having reduced cold flow.

1. BACKGROUND OF THE INVENTION

In the following, the term "plaster" is intended to mean self-adhering, flat coverings which are to be applied to the human skin. The plasters can be of a single- or multi-layer construction and can consist of films, woven fabrics or non-woven fabrics in combination with self-adhering polymers. In addition, the plasters can contain any desired pharmaceutical or cosmetic active agents or also be free of active agent. They can be applied to healthy or damaged skin.

The adhesive of the plasters generally exhibits a flowability which is sufficient so that it can flow around unevennesses or roughnesses of the skin and ther by result in a good bond to the skin. Very "hard" adhesives which have glass transition temperatures of more than 10 to 20° C. usually do not adhere well to the skin. On the other hand, however, if the adhesive exhibits good flow behavior, a small amount of adhesive can escape at the cut edges of the final plaster during storage or when it is worn (so-called "cold flow"). The adhesive which has escaped can, e.g., adhere to the packaging material during storage or adhere to the surrounding clothing or other articles which are in contact to the skin during the duration of application to the skin.

After having been worn for some time such plasters exhibit a cosmetically very displeasing "dirty fringe" which is generally formed by fibers of clothing or other particles which adhere to the adhesive composition which escapes at the cut edge. The dirty fringe can occur directly on the skin outside of the plaster or under the external edges of the plaster.

SUMMARY OF THE INVENTION

The object of the invention is to eliminate these deficiencies connected to the state of the art.

This object is achieved according to the invention by a plaster having reduced cold flow with the features recited in claim 1.

Further advantageous embodiments are subject matter of the dependent claims.

2. DETAILED DESCRIPTION OF THE INVENTION

The above described disadvantages of the state of the art are avoided by the combination of at least two adhesives which are applied to the plaster in a spatially separated manner.

To this end, the layer of adhesive of the actual plaster ("inner layer of adhesive" or "plaster core"; also abbreviated as "core") which, e.g., contains a pharmaceutically active agent is surrounded with a second layer of adhesive ("outer layer of adhesive" or "ring of adhesive"; also abbreviated as "ring") which mechanically prevents that the adhesive of the inner layer escapes. It is clear that this "ring", as long as it fulfills its function, can have any form and, for example, when viewed from above, can be circular, oval or even square or rectangular, and optionally have rounded edges. The skilled person chooses the suitable form according to the practical conditions.

Generally, the inner layer of adhesive of rendered sufficiently flowable and tacky by pharmaceutical or cosmetic active agents or other additives such as resins or plasticizers, so that the inner layer of adhesive provides a good and permanent bond to the skin.

In contrast thereto, the outer layer of adhesive possesses stronger cohesion and thus lower flowability than the inner layer of adhesive because plasticizing additives are missing or are contained in a lesser amount or because it consists of a different polymer or mixture of polymers which does not flow to such a high extent. Thus, cold flow at the cut edge of the plaster is prevented or reduced to such an extent that adherence to the packaging material or occurrence of a dirty fringe on the skin, if the plaster is worn for a longer time, can be reduced or even prevented. Simultaneously, the flowable inner layer of adhesive is mechanically prevented from escaping.

According to the simplest case in the prior art, plasters are prepared by applying a solution or dispersion of adhesive onto a film, woven fabric or non-woven fabric by spreading, spraying, printing or the like and this layer of adhesive is covered with a second film, woven fabric or non-woven fabric after drying. Then, forming of the plaster by die-cutting or cutting and subsequently packaging follows.

In contrast thereto, the plasters according to the invention having reduced cold flow can be, for example, prepared as follows.

2.1 Direct Coating 2.1.1 Preparation of the Plaster Cores

A siliconized film or paper (which, according to its function, in the following is also referred to as "release liner") is coated with the material of the plaster core in a suitable coating machine and subsequently covered with a thin cover film. The plaster cores are die-cut by a die-cutting machine, whereby the die-cutter is to be adjusted so that the siliconized film is not die-cut (e.g., by using the kiss-cut method), i.e. the cores remain on the film. Then the film is wound up.

2.1.2. Preparation of the Plasters with Cores and Rings of Adhesive

The wound film of 2.1.1 with the plaster cores adhering thereto is further coated with the material of the ring of adhesive in a coating machine so that the voids between the cores are filled with the materialo of the ring. Coating is conducted in such a manner that the cover film of the plaster cores is only coated to a minimal extent. After drying (if necessary), the layer of adhesive between the cores should possess the same thickness as the total thickness of the plaster cores. Optionally, coating is repeated as many times as necessary until the thickness has reached the desired value. Then, a second cover film is applied as a cover so that this film uniformly covers both the material of the ring of adhesive as well as the cover film of the plaster core.

In a further die-cutting step, the final plasters are then die-cut out of the laminate. In this step, die-cutting tools are used having a diameter which corresponds to the diameter of the plaster cores plus twice the breadth of the ring of adhesive.

2.2 Separate Direct Coating

According to this embodiment plaster cores, rings of adhesive and a common, adhesive-coated cover film are prepared separately. The cover film connects the plaster cores and rings of adhesive in subsequent step.

2.2.1 Preparation of the Plaster Cores

The preparation corresponds to the preparation in 2.1.1.

2.2.2 Preparation of the Rings of Adhesive

A siliconized film or paper is coated with the material of the ring of adhesive in a suitable coating machine and subsequently covered with a thin cover film. Rings of adhesive are die-cut by a die-cutting machine, whereby the die-cutter is to be adjusted so that the siliconized film is not die-cut, i.e. the rings remain on the film. Then the film is wound up.

2.2.3 Preparation of the Adhesive-coated Cover Film

A thin, non-siliconized film or film siliconized on one side (e.g., Hostaphan MN 15) is coated with a layer of pressure-sensitive adhesive, for example, a hot melt PSA or a UV cross-linked PSA, at a coating weight of approximately 1 to 20 g/m². This coating step can be conducted in a separate coater or directly in the die-cutting and packaging line before mounting the core and the ring.

2.2.4 Preparation of the Final Plasters

The pressure-sensitive adhesive-coated cover film of 2.2.3 is introduced into a appropriate die-cutting line for plasters. The release liner carrying, e.g., the cores, is introduced from a feed roll in such a manner that the cover film of the cores is contacted with the layer of adhesive of the cover film of 2.2.3 and they are bonded together by pressure (e.g., by using a pressure roll). The release linear of the cores is discarded. Then the release liner with the rings of introduced from a second feed roll so that the rings are applied concentrically around the cores.

The release liner of the rings remains on the final product. After lamination, the final plasters are die-cut, e.g., with a contoured die-cutter and then packaged.

2.3 Coating with Masking Films

The actual adhesive composition of the plaster, e.g., with incorporated active agents, is applied to a film, woven fabric or non-woven fabric in the desired size minus the size of the surrounding ring of adhesive, which is subsequently applied, by a printing, coating or spraying process and optionally dried or allowed to solidify.

If coating is conducted by spreading, a mask is applied, e.g., on a siliconized film (release liner), by lamination before coating with the desired adhesive mixture.

Preparation of the Perforated Masking Film

The perforated mask is prepared by applying a thin layer of a pressure-sensitive adhesive, which is also used for the subsequent ring of adhesive, on a paper film or polymer film which is siliconized on both sides (intermediate liner 1). The coating thickness is approximately 1 to 20 g/m². After coating, holes having the size and form which fulfill the requirements of the subsequent inner areas (plaster cores) of the final plasters are die-cut into the film in a suitable die-cutting or cutting apparatus. The thickness of the film including the dried layer of adhesive must correspond exactly to the wet layer thickness of the desired plasters if the subsequent coating of the plaster cores is to be conducted by a solvent process otherwise the thickness must correspond to the dry layer thickness.

Preparation of the Plaster Cores

After coating, the siliconized side of the release liner is covered with the perforated masking film.

Then, the resultant laminate is further coated by filling the openings which had been left free in the perforated masking film with the material of the plaster cores. After drying of the fillings (if necessary), the laminate is wound up.

Preparation of the Plasters having Cores and Rings of Adhesives

In a suitable coating machine, the perforated masking film is removed from the release liner of the cores and the film (now carrying the cores on its silicone side) is coated again, namely in such a way that the material of the ring of adhesive fills the voids between the cores. The thickness of the coating is chosen according to the thickness of the cores taking the shrinking factor of the layer into consideration. After drying or hardening of the material of the ring the same thickness of the layer as that of the cores should result as far as possible.

After leaving the coater, the compound layer of adhesive is covered with a non-siliconized cover film.

The final plasters are now die-cut out of the laminate in a further die-cutting step. In this step, die-cutting tools are employed having a diameter which corresponds to the diameter of the plaster cores plus twice the breadth of the ring of adhesive.

2.4 Preparation by Covering with Adhesive

In a further embodiment, the plaster cores are first prepared as described in 2.2.1. Subsequently, the release liner carrying the cores is completely covered with an adhesive-coated cover film which is described in 2.2.3. Then, the final plasters are die-cut. In this step, die-cutting tools are used having a diameter with corresponds to the diameter of the plaster cores plus twice the breadth of the ring of adhesive.

The invention claimed is:

1. A flat self-adhering plaster having reduced cold flow, consisting of a cover, a layer of adhesive which attaches to skin having a core of adhesive made flowable by a plasticizing additive, a ring of adhesive free of a plasticizing additive, wherein the adhesive of said ring has a reduced flowability and stronger cohesion to skin to that of said core, wherein said ring surrounds said core, and wherein said core is the only pharmaceutical or cosmetic active agent area, and a removable carrier.

2. A plaster according to claim 1, wherein removable carrier acts as a temporary cover and which is present on a side of the layer of adhesive opposite the cover.

3. A plaster according to claim 1, wherein the cover consists essentially of a film of plastic, woven fabric or non-woven fabric.

4. A plastic according to claim 2, wherein the carrier consists essentially of a film of plastic, paper or a laminate thereof.

5. A plaster according to claim 3, wherein the film of plastic consists essentially of a film of polyethylene terephthalate, polyethylene, polypropylene or polyvinyl chloride.

6. A plastic according to claim 4, wherein the carrier possesses a release coating.

7. A plastic according to claim 6, wherein the release coating consists essentially of a silicone layer or fluoro-silicone layer.

8. The plaster according to claim 1, wherein the plasticizing additive is selected from the group consisting of pharmaceutical agents, cosmetic active agents, resins and plasticizers.

9. A flat self-adhering plaster having reduced cold flow, consisting of a layer of adhesive adapted to attach to skin and comprising a core of flowable adhesive comprised of a polymer or a mixture of polymers, and a ring of adhesive being an adhesive having reduced flowability to that of the core, wherein said ring of adhesive is comprised of a different polymer or different mixture of polymers from that of said core, and wherein said ring surrounds said core.

* * * * *